(12) United States Patent
Lee et al.

(10) Patent No.: US 8,921,083 B2
(45) Date of Patent: Dec. 30, 2014

(54) MODIFIED MICROORGANISM FOR HIGH EFFICIENT PRODUCTION OF 1,4-BUTANEDIOL

(71) Applicant: Samsung Electronics Co., Ltd., Suwon-si (KR)

(72) Inventors: Woo Yong Lee, Hwaseong-si (KR); Hyun Min Koo, Seoul (KR); Sung Soo Kim, Hwaseong-si (KR); Jae Young Kim, Suwon-si (KR); Jae Chan Park, Yongin-si (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 0 days.

(21) Appl. No.: 13/946,179

(22) Filed: Jul. 19, 2013

(65) Prior Publication Data

US 2014/0030773 A1   Jan. 30, 2014

(30) Foreign Application Priority Data

Jul. 25, 2012  (KR) .................... 10-2012-0081199

(51) Int. Cl.

| | | |
|---|---|---|
| *C07K 14/34* | (2006.01) | |
| *C12N 15/77* | (2006.01) | |
| *C12P 7/18* | (2006.01) | |
| *C12P 7/62* | (2006.01) | |
| *C08G 63/16* | (2006.01) | |
| *C08G 63/183* | (2006.01) | |
| *C12N 9/90* | (2006.01) | |
| *C12N 9/10* | (2006.01) | |

(52) U.S. Cl.
CPC . *C12P 7/18* (2013.01); *C08G 63/16* (2013.01); *C12N 9/90* (2013.01); *C07K 14/34* (2013.01); *C12P 7/62* (2013.01); *C12N 15/77* (2013.01); *C08G 63/183* (2013.01); *C12N 9/1029* (2013.01)
USPC ....... 435/158; 435/135; 435/252.32; 435/471

(58) Field of Classification Search
None
See application file for complete search history.

(56) References Cited

U.S. PATENT DOCUMENTS

| | | | |
|---|---|---|---|
| 2007/0059744 | A1 | 3/2007 | Pompejus et al. |
| 2007/0059809 | A1 | 3/2007 | Pompejus et al. |
| 2009/0047719 | A1 | 2/2009 | Burgard et al. |
| 2011/0014669 | A1 | 1/2011 | Madden et al. |

FOREIGN PATENT DOCUMENTS

| | | |
|---|---|---|
| EP | 1108790 A2 | 6/2001 |
| KR | 1020070096348 A | 10/2007 |
| KR | 1020090025902 A | 3/2009 |

*Primary Examiner* — Suzanne M Noakes
*Assistant Examiner* — Gerard Lacourciere
(74) *Attorney, Agent, or Firm* — Leydig, Voit & Mayer, Ltd.

(57) ABSTRACT

A modified microorganism for producing a high yield of 1,4-butanediol, and a method of producing 1,4-butanediol using the modified microorganism, wherein the modified microorganism is altered so as to delete or disrupt expression of at least one of transcription regulatory factor NCgl2886, GCN5-related N-acetyltransferase NCgl2090, hypothetical protein NCgl0224 or sugar phosphate isomerase/epimerase NCgl2956.

18 Claims, 3 Drawing Sheets

SEQUENCE LISTING

```
<160> NUMBER OF SEQ ID NOS: 5

<210> SEQ ID NO 1
<211> LENGTH: 157
<212> TYPE: PRT
<213> ORGANISM: Artificial Sequence
<220> FEATURE:
<223> OTHER INFORMATION: Synthetic (A48_NCgl2886_Transcription_factor)

<400> SEQUENCE: 1

Met Leu Ala Gly Met Pro Asn Leu Asn Ala Glu Glu Leu Ala Val Arg
1               5                   10                  15

Val Arg Pro Ala Leu Thr Lys Leu Tyr Val Leu Tyr Phe Arg Arg Ser
                20                  25                  30

Val Asn Ser Asp Leu Ser Gly Pro Gln Leu Thr Ile Leu Ser Arg Leu
            35                  40                  45

Glu Glu Asn Gly Pro Ser Arg Ile Ser Arg Ile Ala Glu Leu Glu Asp
        50                  55                  60

Ile Arg Met Pro Thr Ala Ser Asn Ala Leu His Gln Leu Glu Gln Leu
65                  70                  75                  80

Asn Leu Val Glu Arg Ile Arg Asp Thr Lys Asp Arg Arg Gly Val Gln
                85                  90                  95

Val Gln Leu Thr Asp His Gly Arg Glu Glu Leu Glu Arg Val Asn Asn
            100                 105                 110

Glu Arg Asn Ala Glu Met Ala Arg Leu Leu Glu Met Leu Thr Pro Glu
        115                 120                 125

Gln Leu Glu Arg Thr Glu Asp Leu Val Asp Ile Ile Thr Glu Leu Ala
    130                 135                 140

Glu Val Tyr Gly Ser Trp Lys Glu Thr Asp Ser Gly Ser
145                 150                 155

<210> SEQ ID NO 2
<211> LENGTH: 164
<212> TYPE: PRT
<213> ORGANISM: Artificial Sequence
<220> FEATURE:
<223> OTHER INFORMATION: Synthetic (F22_NCgl2090_GCN5-related_N-
      acetyltransferase)

<400> SEQUENCE: 2

Met Asn Thr Glu Glu Asp Gly Leu Ser Phe Ala Val Thr Ala Thr Leu
1               5                   10                  15

Val Glu Gly Lys Trp Gln Val Arg Glu Phe Glu Asp His Phe Ser Lys
                20                  25                  30

Leu Ser Thr Ser Ile Asn Ala Val Arg Ser Leu Arg Ser Glu Gly Pro
            35                  40                  45

Ala Phe Ala Leu Leu Cys Val Asp Asp Glu Tyr Phe Val Met Val Arg
        50                  55                  60
```

```
Pro Thr Pro Ser Arg Val Phe Leu Phe Leu Ser Asp Ala Pro Met Ala
 65                  70                  75                  80

Val Asp Asp Asp Phe Ala Ala Ala Val Met Asp Glu Leu Asp Ala Asp
                 85                  90                  95

Leu Pro Asp Ile Asn Pro Asp Asp Leu Asp Asp Ile Asp Pro Trp Pro
            100                 105                 110

Glu Gly Asp Phe Asp Ile Leu Ala Asp Leu Gly Leu Ser Glu Glu Val
            115                 120                 125

Leu Ser Val Ile Cys Asp Asp Met Asp Leu Asp Pro Ser Glu Gln Leu
130                 135                 140

Leu Arg Ile Ala Glu Glu Leu Gly Phe Asp Asn Asp Leu Ala Arg Val
145                 150                 155                 160

Val Gly Phe Asp

<210> SEQ ID NO 3
<211> LENGTH: 296
<212> TYPE: PRT
<213> ORGANISM: Artificial Sequence
<220> FEATURE:
<223> OTHER INFORMATION: Synthetic (F66_NCgl0224_Hypothetical_protein)

<400> SEQUENCE: 3

Met Lys Pro Gln Leu Ile Ala Ser Cys Trp Thr Ser Ala Gly Asp Ala
1                5                  10                  15

Ala Pro Asp Arg Asp Asp Leu Ser Pro Val Ala Ile Asp Glu Arg
                 20                  25                  30

Ile Ala Leu Val Ala Glu Thr Gly Trp Ala Gly Ile Gly Leu Val His
            35                  40                  45

Ala Asp Leu Ile Lys Ala Arg Asp Thr Ile Gly Tyr Glu Glu Leu Arg
        50                  55                  60

Arg Arg Ile His Ala Ala Gly Ile Glu Ile Ile Glu Val Glu Phe Leu
65                  70                  75                  80

Asn Gly Trp Trp Ala Thr Gly Ala Glu Arg Gln Glu Ser Asp Ala Val
                 85                  90                  95

Arg Ala Asp Leu Phe Ala Ala Ala Gln Ala Leu Gly Ser Pro His Ile
            100                 105                 110

Lys Val Gly Ala Gly Glu Gly Thr Asn Gly Val Val Pro Ile Ala His
            115                 120                 125

Met Ala Ser Ala Phe Thr Asp Leu Ala Ala Glu Ala Glu Ala His Gly
130                 135                 140

Val Lys Leu Ala Leu Glu Ala Thr Pro Phe Ser His Leu Lys Thr Leu
145                 150                 155                 160

Lys Thr Ile Tyr Asp Ala Leu Glu Val Val Ser His Ser Asp Ser Pro
                 165                 170                 175

Ser Ala Gly Leu Met Val Asp Ile Trp His Thr Ala Lys Ile Gly Ile
            180                 185                 190

Pro Asn Asp Glu Leu Trp Arg Asn Ile Pro Leu Ser Lys Val Asn Ala
        195                 200                 205

Val Glu Val Asp Asp Gly Phe Ile Asp Thr Pro Ile Asp Leu Phe Asp
    210                 215                 220

Asp Ser Thr Asn Arg Arg Ala Tyr Cys Gly Glu Gly Glu Phe Asp Pro
225                 230                 235                 240

Ala Ser Phe Ile Arg Gly Ala Ile Asp Ala Gly Trp Thr Gly Ala Tyr
                 245                 250                 255
```

```
Gly Val Glu Ile Ile Ser Ala Glu His Arg Ser Leu Pro Val Lys Glu
            260                 265                 270

Gly Leu Gln Arg Ala Phe Asp Thr Thr Ile Ala Ala Phe Glu Gln Ala
        275                 280                 285

Ala Arg Leu Ala Pro Ser Thr Asn
    290                 295

<210> SEQ ID NO 4
<211> LENGTH: 296
<212> TYPE: PRT
<213> ORGANISM: Artificial Sequence
<220> FEATURE:
<223> OTHER INFORMATION: Synthetic
      (G65_NCgl2956_Sugar_phosphate_isomerase_epimerase)

<400> SEQUENCE: 4

Met Lys Pro Gln Leu Ile Ala Ser Cys Trp Thr Ser Ala Gly Asp Ala
1               5                   10                  15

Ala Pro Asp Arg Asp Asp Leu Ser Ser Pro Val Ala Ile Asp Glu Arg
            20                  25                  30

Ile Ala Leu Val Ala Glu Thr Gly Trp Ala Gly Ile Gly Leu Val His
        35                  40                  45

Ala Asp Leu Ile Lys Ala Arg Asp Thr Ile Gly Tyr Glu Glu Leu Arg
    50                  55                  60

Arg Arg Ile His Ala Ala Gly Ile Glu Ile Ile Glu Val Glu Phe Leu
65                  70                  75                  80

Asn Gly Trp Trp Ala Thr Gly Ala Glu Arg Gln Glu Ser Asp Ala Val
                85                  90                  95

Arg Ala Asp Leu Phe Ala Ala Ala Gln Ala Leu Gly Ser Pro His Ile
            100                 105                 110

Lys Val Gly Ala Gly Glu Gly Thr Asn Gly Val Val Pro Ile Ala His
        115                 120                 125

Met Ala Ser Ala Phe Thr Asp Leu Ala Ala Glu Ala Glu Ala His Gly
    130                 135                 140

Val Lys Leu Ala Leu Glu Ala Thr Pro Phe Ser His Leu Lys Thr Leu
145                 150                 155                 160

Lys Thr Ile Tyr Asp Ala Leu Glu Val Val Ser His Ser Asp Ser Pro
                165                 170                 175

Ser Ala Gly Leu Met Val Asp Ile Trp His Thr Ala Lys Ile Gly Ile
            180                 185                 190

Pro Asn Asp Glu Leu Trp Arg Asn Ile Pro Leu Ser Lys Val Asn Ala
        195                 200                 205

Val Glu Val Asp Asp Gly Phe Ile Asp Thr Pro Ile Asp Leu Phe Asp
    210                 215                 220

Asp Ser Thr Asn Arg Arg Ala Tyr Cys Gly Glu Gly Glu Phe Asp Pro
225                 230                 235                 240

Ala Ser Phe Ile Arg Gly Ala Ile Asp Ala Gly Trp Thr Gly Ala Tyr
                245                 250                 255

Gly Val Glu Ile Ile Ser Ala Glu His Arg Ser Leu Pro Val Lys Glu
            260                 265                 270

Gly Leu Gln Arg Ala Phe Asp Thr Thr Ile Ala Ala Phe Glu Gln Ala
        275                 280                 285

Ala Arg Leu Ala Pro Ser Thr Asn
    290                 295
```

<210> SEQ ID NO 5
<211> LENGTH: 2001
<212> TYPE: DNA
<213> ORGANISM: Artificial Sequence
<220> FEATURE:
<223> OTHER INFORMATION: Synthetic (EpiCentre Corp, EZ-Tn5 Tnp
      Transposome Kit)

<400> SEQUENCE: 5

```
ctgtctctta tacacatctc aaccatcatc gatgaattgc ttcgttaata cagatgtagg      60
tgttccacag ggtagccagc agcatcctgc gatgcagatc cggatgccat ttcattacct     120
ctttctccgc acccgacata gatccgaaga tcagcagttc aacctgttga tagtacgtac     180
taagctctca tgtttcacgt actaagctct catgtttaac gtactaagct ctcatgttta     240
acgaactaaa ccctcatggc taacgtacta agctctcatg ctaacgtac taagctctca      300
tgtttcacgt actaagctct catgtttgaa caataaaatt aatataaatc agcaacttaa     360
atagcctcta aggttttaag ttttataaga aaaaaagaa tatataaggc ttttaaagct       420
tttaaggttt aacggttgtg acaacaagc cagggatctg ccatttcatt acctctttct      480
ccgcacccga catagatccg aacataatg gtgcagggcg ctgacttccg cgtttccaga      540
ctttacgaaa cacggaaacc gaagaccatt catgttgttg ctcaggtcgc agacgttttg     600
cagcagcagt cgcttcacgt tcgctcgcgt atcggtgatt cattctgcta accagtaagg     660
caaccccgcc agcctagccg ggtcctcaac gacaggagca cgatcatgcg cacccgtggc     720
caggacccaa cgctgcccga gatgcgccgc gtgcggctgc tggagatggc ggacgcgatg     780
gatatgttct gccaagggtt ggtttgcgca ttcacagggt gtctcaaaat ctctgatgtt     840
acattgcaca agataaaaat atatcatcat gaacaataaa actgtctgct tacataaaca     900
gtaatacaag gggtgttatg agccatattc aacgggaaac gtcttgctcg aggccgcgat     960
taaattccaa catggatgct gatttatatg ggtataaatg gctcgcgat aatgtcgggc     1020
aatcaggtgc gacaatctat cgattgtatg ggaagcccga tgcgccagag ttgtttctga    1080
aacatggcaa aggtagcgtt gccaatgatg ttacagatga gatggtcaga ctaaactggc    1140
tgacggaatt tatgcctctt ccgaccatca agcattttat ccgtactcct gatgatgcat    1200
ggttactcac cactgcgatc cccggaaaaa cagcattcca ggtattagaa gaatatcctg    1260
attcaggtga aaatattgtt gatgcgctgg cagtgttcct gcgccggttg cattcgattc    1320
ctgtttgtaa ttgtcctttt aacagcgatc gcgtatttcg tctcgctcag gcgcaatcac    1380
gaatgaataa cggtttggtt gatgcgagtg attttgatga cgagcgtaat ggctggcctg    1440
ttgaacaagt ctggaaagaa atgcataaac ttttgccatt ctcaccggat tcagtcgtca    1500
ctcatggtga tttctcactt gataacctta ttttgacga ggggaaatta ataggttgta     1560
ttgatgttgg acgagtcgga atcgcagacc gataccagga tcttgccatc ctatggaact    1620
gcctcggtga gttttctcct tcattacaga acggcttttt caaaaatat ggtattgata      1680
atcctgatat gaataaattg cagtttcatt tgatgctcga tgagttttc taatcagaat      1740
tggttaattg gttgtaacac tggcagagca ttacgctgac ttgacgggac ggcggctttg    1800
ttgaataaat cgaacttttg ctgagttgaa ggatcagatc acgcatcttc ccgacaacgc    1860
agaccgttcc gtggcaaagc aaaagttcaa aatcaccaac tggtccacct acaacaaagc    1920
tctcatcaac cgtggcgggg atcctctaga gtcgacctgc aggcatgcaa gcttcagggt    1980
tgagatgtgt ataagagaca g                                              2001
```

MODIFIED MICROORGANISM FOR HIGH EFFICIENT PRODUCTION OF 1,4-BUTANEDIOL

CROSS-REFERENCE TO RELATED APPLICATION

This application claims priority to Korean Patent Application No. 10-2012-0081199, filed on Jul. 25, 2012, and all the benefits accruing therefrom under 35 U.S.C. §119, the content of which in its entirety is herein incorporated by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 11,448 Bytes ASCII (Text) file named "711396_ST25.TXT," created on Jul. 9, 2013.

BACKGROUND 1,4-Butanediol (1,4-BDO) has been produced at a scale of approximately 1,000,000 tons or more all over the world, and used for various applications such as production of γ-butyrolactone (GBL), tetrahydrofuran (THF), pyrrolidone, N-methylpyrrolidone (NMP), etc.

1,4-Butanediol may be used as a monomer such as an acrylonitrile butadiene styrene (ABS) copolymer and polyurethane (PU), and may be converted into tetrahydrofuran, which may be used as a raw material for spandex fibers such as polytetramethylene ether glycol (PTMEG).

Meanwhile, *Corynebacterium glutamicum* is a gram-positive strain which has been used for production of amino acids such as glutamic acid, lysine, threonine, isoleucine, etc. *C. glutamicum* has advantages in that its growth conditions are easily adjusted, it grows fast, and it is not easily mutated due to the stability of its genetic structure. Also, *C. glutamicum* is not detrimental to the environment since it is a non-pathogenic strain and does not form spores. In particular, attention has been drawn to the use of *C. glutamicum* in the related industries since *C. glutamicum* may be cultured at a concentration 4 times higher than that of *E. coli*.

SUMMARY

In an aspect, a modified microorganism for producing a high yield of 1,4-butanediol, wherein the modified microorganism is genetically engineered to disrupt or delete a gene of the non-modified microorganism, wherein the gene encodes at least one selected from the group consisting of transcription regulatory factor NCg12886, GCN5-related N-acetyltransferase NCg12090, hypothetical protein NCg10224 and sugar phosphate isomerase/epimerase NCg12956, is provided. In another aspect, a method of producing 1,4-butanediol using the modified microorganism is provided. The method may include culturing the modified microorganism in a glucose-containing medium, and recovering 1,4-butanediol from the medium. The modified microorganism may produce a high yield of 1,4-butanediol even in the presence of high-concentration 1,4-butanediol due to an increase in tolerance of the 1,4-butanediol.

Also provided is a method of increasing the yield of 1,4-butanediol from a microorganism, the method comprising deleting or disrupting the expression of transcription regulatory factor NCg12886, GCN5-related N-acetyltransferase NCg12090, hypothetical protein NCg10224, or sugar phosphate isomerase/epimerase NCg12956 in the microorganism, whereby the 1,4-butanediol yield of the microorganism is increased as compared to a wild-type microorganism of the same kind.

Also provided is a method of producing polybutylene succinate (PBS), comprising: culturing the modified microorganism in a glucose-containing medium; recovering the 1,4-butanediol from the medium; and performing condensation polymerization of the recovered 1,4-butanediol with succinic acid or dimethyl-succinate, thereby producing PBS.

Also provided is a method of producing polybutylene terephthalate (PBT), comprising: culturing the modified microorganism of claim 1 in a glucose-containing medium; recovering the 1,4-butanediol from the medium; and performing condensation polymerization of the recovered 1,4-butanediol with terephthalic acid or dimethyl-terephthalate, thereby producing PBT.

BRIEF DESCRIPTION OF THE DRAWINGS

The above and other aspects of this disclosure will become more readily apparent by describing in further detail non-limiting exemplary embodiments thereof with reference to the accompanying drawings, in which.

DETAILED DESCRIPTION

Unless otherwise indicated, the practice of the disclosure involves conventional techniques commonly used in molecular biology, microbiology, protein purification, protein engineering, protein and DNA sequencing, and recombinant DNA fields, which are within the skill of the art. Such techniques are known to those of skill in the art and are described in numerous standard texts and reference works.

Unless defined otherwise herein, all technical and scientific terms used herein have the same meaning as commonly understood by one of ordinary skill in the art to which this disclosure belongs. Various scientific dictionaries that include the terms included herein are well known and available to those in the art. Although any methods and materials similar or equivalent to those described herein find use in the practice or testing of the disclosure, some preferred methods and materials are described. Accordingly, the terms defined immediately below are more fully described by reference to the specification as a whole. It is to be understood that this disclosure is not limited to the particular methodology, protocols, and reagents described, as these may vary, depending upon the context in which they are used by those of skill in the art.

As used herein, the singular terms "a", "an," and "the" include the plural reference unless the context clearly indicates otherwise. Unless otherwise indicated, nucleic acids are written left to right in 5' to 3' orientation and amino acid sequences are written left to right in amino to carboxyl orientation, respectively.

Numeric ranges are inclusive of the numbers defining the range. It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The headings provided herein are not limitations of the various aspects or embodiments of the invention which can be had by reference to the specification as a whole.

To produce 1,4-butanediol at a high yield, a modified microorganism having a tolerance to 1,4-butanediol is provided.

There have been attempts to manufacture a chemical material such as 1,4-butanediol through fermentation which is a biological production process. Fermentation is performed by various kinds of bacterial species that consume sugars and convert the sugars into a desired chemical material. Development of yeast or fungal biocatalysts used to manufacture a chemical material from sugars has been carried out for the following reasons. Many bacteria cannot synthesize certain amino acids or proteins required to effectively metabolize sugars for their growth. As a result, the bacteria should be fed often with somewhat complicated nutriments. This causes a direct increase in cost required to perform fermentation. An increase in complexity of media makes it difficult to recover a fermentation product in a rationally pure state. Thus, additional operations and costs are required to recover the fermentation product. On the other hand, many yeast species can synthesize amino acids or proteins that are essential for their growth from an inorganic nitrogen compound. In general, these yeast species grow well and ferment in a so-called "defined" medium. Here, the medium is generally less expensive, and causes less difficulty in recovering the products.

Another reason for which attention has been drawn to yeast as a biocatalyst for producing a chemical material is related to characteristics of a product itself. To find an economically practical method, a high concentration of a chemical product has to be accumulated in a fermentation medium. When the fermentation product is present at a high concentration, it may often be toxic to the biocatalyst. As a larger amount of the chemical material is produced, the toxicity will gradually increase in the medium. Most of the bacteria producing the chemical material do not grow well in toxic environments, do not survive under the toxic conditions, or produce products too slowly to be economically practical. Therefore, the chemical materials produced thereafter have to be recovered.

When a biocatalyst effectively grows in the presence of a higher concentration of the chemical material, it is possible to produce a great quantity of the chemical material within a short period of time.

In an aspect, a modified microorganism for producing a high yield of 1,4-butanediol, in which a gene encoding at least one selected from the group consisting of transcription regulatory factor NCgl2886, GCN5-related N-acetyltransferase NCgl2090, hypothetical protein NCgl0224 and sugar phosphate isomerase/epimerase NCgl2956 is deleted or disrupted (inactivated), is provided. In other words, the microorganism comprises a genetic alteration that disrupts or deletes the expression of one or more of the foregoing genes. In a related aspect, a method of increasing the yield of 1,4-butanediol from a microorganism is provided, the method comprising deleting or disrupting the expression of transcription regulatory factor NCgl2886, GCN5-related N-acetyltransferase NCgl2090, hypothetical protein NCgl0224, or sugar phosphate isomerase/epimerase NCgl2956 in the microorganism, whereby the 1,4-butanediol yield of the microorganism is increased as compared to a wild-type microorganism of the same kind.

Figure 1:
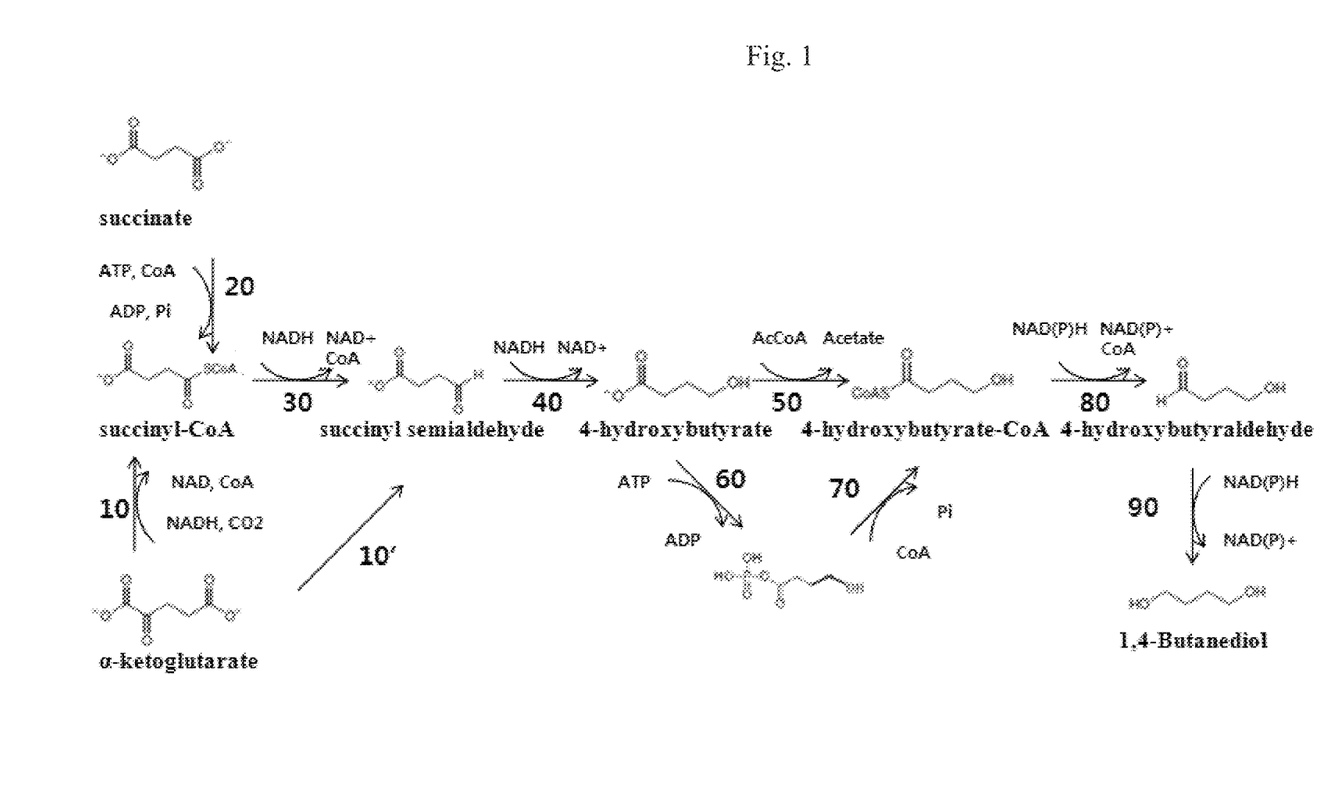
FIG. 1 is a schematic illustration of the 1,4-butanediol biosynthetic pathway.

The term "1,4-butanediol" used in this specification refers to an organic compound which is represented by the formula $C_4H_{10}O_2$ (hereinafter, referred to as "1,4-butanediol") and may be produced through two steps. The biosynthetic pathway of 1,4-butanediol is shown in FIG. 1.

In Step 1, α-ketoglutarate or succinate is converted into 4-hydroxybutyryl-CoA. More particularly, the α-ketoglutarate or succinate may be converted into 4-hydroxybutyryl-CoA via succinyl-CoA, succinyl semialdehyde and 4-hydroxybutyrate. The α-ketoglutarate may be converted into succinyl-CoA by means of α-ketoglutarate dehydrogenase (10), and the succinate may be converted into succinyl-CoA by means of succinyl-CoA transferase (20). The succinyl-CoA is converted into succinyl semialdehyde by means of succinate semialdehyde dehydrogenase (30). Meanwhile, the α-ketoglutarate may be directly converted into succinyl semialdehyde by means of α-ketoglutarate decarboxylase (10') without production of succinyl-CoA. The succinyl semialdehyde is converted into 4-hydroxybutyrate by means of 4-hydroxybutanoate dehydrogenase (40). The 4-hydroxybutyrate may be converted into 4-hydroxybutyryl-CoA by means of 4-hydroxybutyryl-CoA transferase (50). Also, the 4-hydroxybutyrate may be converted into 4-hydroxybutyryl phosphate by means of butyrate kinase (60), and the 4-hydroxybutyryl phosphate may be converted into 4-hydroxybutyryl-CoA by means of phosphotransbutyrylase (70).

In Step 2, the 4-hydroxybutyryl-CoA is converted into 1,4-butanediol via 4-hydroxybutyraldehyde. The 4-hydroxybutyryl-CoA may be converted into 4-hydroxybutyraldehyde by means of aldehyde dehydrogenase (80), and the 4-hydroxybutyraldehyde may be finally converted into 1,4-butanediol by means of alcohol dehydrogenase (90).

The modified microorganism may effectively activate the 1,4-butanediol biosynthetic pathway in the presence of high-concentration 1,4-butanediol since the tolerance to 1,4-butanediol is enhanced by deleting or disrupting a gene encoding at least one selected from the group consisting of transcription regulatory factor NCgl2886, GCN5-related N-acetyltransferase NCgl2090, hypothetical protein NCgl0224 and sugar phosphate isomerase/epimerase NCgl2956.

As used herein, the term "genetically engineered" "metabolically engineered" or "metabolic engineering" involves rational pathway design and assembly of biosynthetic genes, genes associated with operons, and control elements of such nucleic acid sequences, for the production of a desired metabolite, such as an alcohol, in a microorganism. "Metabolically engineered" can further include optimization of metabolic flux by regulation and optimization of transcription, translation, protein stability and protein functionality using genetic engineering and appropriate culture condition. The biosynthetic genes can be heterologous to the host (e.g., microorganism), either by virtue of being foreign to the host, or being modified by mutagenesis, recombination, or association with a heterologous expression control sequence in an endogenous host cell. Appropriate culture conditions are conditions such as culture medium pH, ionic strength, nutritive content, etc., temperature, oxygen, $CO_2$, nitrogen content, humidity, and other culture conditions that permit production of the compound by the host microorganism, i.e., by the metabolic action of the microorganism. Appropriate culture conditions are well known for microorganisms that can serve as host cells.

Accordingly, a metabolically or genetically "engineered" or "modified" microorganism, which can also be called a "recombinant" microorganism, is produced via the introduction of genetic material (including alteration, e.g., mutation or deletion, of endogenous genetic material) into a host or parental microorganism of choice thereby modifying or altering the cellular physiology and biochemistry of the microorganism. Through the introduction of genetic material the parental microorganism acquires new properties, e.g. the ability to produce a new, or greater quantities of, an intracellular metabolite. For example, the introduction of genetic material into a parental microorganism results in a new or modified ability to produce a chemical. The genetic material introduced into the parental microorganism may contain one or more genes, or parts of genes, encoding one or more of the enzymes involved in a biosynthetic pathway for the production of a chemical and may also include additional elements for the expression or regulation of expression of these genes, e.g. promoter sequences.

In one embodiment, the modified microorganism may be, but is not limited to, selected from the group consisting of *Escherichia, Klebsiella, Bacillus, Corynebacterium, Zymomonas, Lactococcus, Lactobacillus, Streptomyces, Clostridium, Pseudomonas, Alcaligenes, Salmonella, Shigella, Burkholderia, Aspergillus, Oligotropha, Pichia, Candida, Hansenula, Saccharomyces*, and *Kluyveromyces*. In an exemplary embodiment, a *Corynebacterium glutamicum* was used.

As used herein, the term "gene" refers to a nucleotide sequence that encodes a gene product, such as a protein or enzyme, including a chromosomal or non-chromosomal segment of DNA involved in producing a polypeptide chain that may or may not include regions preceding and following the coding regions, for example, 5' untranslated ("5' UTR") or leader sequences and 3' untranslated ("3' UTR") or trailer sequences, as well as intervening sequence (introns) between individual coding segments (exons).

As used interchangeably herein, the terms "polynucleotide" and "nucleic acid" refer to a polymeric form of nucleotides of any length. These terms may include, but are not limited to, a single-stranded DNA ("deoxyribonucleic acid"), double-stranded DNA, genomic DNA, cDNA, or a polymer comprising purine and pyrimidine bases, or other natural, chemically-modified, biochemically-modified, non-natural or derivatized nucleotide bases. Non-limiting examples of polynucleotides include genes, gene fragments, chromosomal fragments, ESTs, exons, introns, mRNA, tRNA, rRNA, ribozymes, cDNA, recombinant polynucleotides, branched polynucleotides, plasmids, vectors, isolated DNA of any sequence, isolated RNA ("ribonucleic acid") of any sequence, nucleic acid probes, and primers. It will be understood that, as a result of the degeneracy of the genetic code, a multitude of nucleotide sequences encoding a given protein may be produced.

The phrase "deleted or disrupted" used herein means that the entire coding region of a gene is removed or a gene or a promoter or terminator domain thereof is modified (for example, by deletion, insertion or mutation) so that the gene can no longer produce an active enzyme or can produce an enzyme whose activity is severely lowered. The deletion or disruption may be achieved using a method such as gene manipulation, enforced silencing or mutagenesis and/or selection or screening.

According to one exemplary embodiment, a gene encoding at least one selected from the group consisting of transcription regulatory factor NCgl2886, GCN5-related N-acetyltransferase NCgl2090, hypothetical protein NCgl0224 and sugar phosphate isomerase/epimerase NCgl2956 may be deleted or disrupted in the modified microorganism. The genes can be screened by random mutagenesis using a transposon.

The term "transposon" used herein refers to an insertion sequence element, and means a base sequence that can transpose on the chromosomes or plasmids. The transposon has an activity of sensing and inserting a specific base sequence since transaminase, referred to as transposase, is present in the transposon. Several hundreds of transposons have been known in a variety of bacteria (TRANSPOSON-BASED STRATEGIES FOR MICROBIAL FUNCTIONAL GENOMICS AND PROTEOMICS (2003) Annual Review of Genetics 37: 3-29 Finbarr Hayes).

According to the exemplary embodiments, the transposon is not particularly limited. According to one exemplary embodiment, a transposon having the base sequence of SEQ ID NO: 5 can be used (e.g., Transposon (EpiCentre, EZ-Tn5™ <R6Kγori/KAN-2>Tnp Transposome™ Kit).

The transcription regulatory factor NCgl2886 may include the amino acid sequence of SEQ ID NO: 1, or a sequence with at least about 70%, at least about 75%, at least about 80%, at least about 85%, at least about 90%, at least about 92%, at least about 95%, at least about 97%, at least about 98% or at least about 99% sequence identity to the amino acid sequence of SEQ ID NO: 1.

The GCN5-related N-acetyltransferase NCgl2090 may include the amino acid sequence of SEQ ID NO: 2, or a sequence with at least about 70%, at least about 75%, at least about 80%, at least about 85%, at least about 90%, at least about 92%, at least about 95%, at least about 97%, at least about 98% or at least about 99% sequence identity to the amino acid sequence of SEQ ID NO: 2.

The hypothetical protein NCgl0224 may include the amino acid sequence of SEQ ID NO: 3, or a sequence with at least about 70%, at least about 75%, at least about 80%, at least about 85%, at least about 90%, at least about 92%, at least about 95%, at least about 97%, at least about 98% or at least about 99% sequence identity to the amino acid sequence of SEQ ID NO: 3.

The sugar phosphate isomerase/epimerase NCgl2956 may include the amino acid sequence of SEQ ID NO: 4, or a sequence with at least about 70%, at least about 75%, at least about 80%, at least about 85%, at least about 90%, at least about 92%, at least about 95%, at least about 97%, at least about 98% or at least about 99% sequence identity to the amino acid sequence of SEQ ID NO: 4.

As used herein, the term "identity" refers to sequence similarity or sequence homology. This homology or identity (e.g., percent identity) may be determined using standard techniques known in the art (See e.g., Smith and Waterman, Adv. Appl. Math., 2:482 [1981]; Needleman and Wunsch, J. Mol. Biol., 48:443 [1970]; Pearson and Lipman, Proc. Natl. Acad. Sci. USA 85:2444 [1988]; programs such as GAP, BESTFIT, FASTA, and TFASTA in the Wisconsin Genetics Software Package (Genetics Computer Group, Madison, Wis.); and Devereux et al., Nucl. Acid Res., 12:387-395 [1984]).

In an embodiment, the gene encoding at least one selected from the group consisting of transcription regulatory factor NCgl2886, GCN5-related N-acetyltransferase NCgl2090, hypothetical protein NCgl0224 and sugar phosphate isomerase/epimerase NCgl2956 may be native or heterologous to a host strain.

As used herein, the term "heterologous" means that a genetic material of interest is not natural in a host strain. The term "native" means that a genetic material is found in a genome of a wild-type cell in the host strain.

As used herein, the term "derived from" means that a genetic material is wholly or partially isolated from its given source or purified from the given source.

The gene encoding at least one selected from the group consisting of transcription regulatory factor NCgl2886, GCN5-related N-acetyltransferase NCgl2090, hypothetical protein NCgl0224 and sugar phosphate isomerase/epimerase NCgl2956 may be derived from all of prokaryotic and eukaryotic organisms such as archaebacteria, eubacteria, yeasts, plants, insects, animals and humans. For example, the microorganism may be at least one selected from the group consisting of *Escherichia coli*, *Saccharomyces cerevisiae*, *Clostridium kluyveri*, *Clostridium acetobutylicum*, *Clostridium beijerinckii*, *Clostridium saccharoperbutylacetonicum*, *Clostridium perfringens*, *Clostridium difficile*, *Ralstonia eutropha*, *Mycobacterium bovis*, *Mycobacterium tuberculosis*, *Porphyromonas gingivalis* and *Corynebacterium glutamicum*, but is not limited thereto.

In one embodiment, the gene encoding at least one selected from the group consisting of transcription regulatory factor NCgl2886, GCN5-related N-acetyltransferase NCgl2090, hypothetical protein NCgl0224 and sugar phosphate isomerase/epimerase NCgl2956 derived from *Corynebacterium glutamicum* are used herein.

In another embodiment, a method of producing 1,4-butanediol using the modified microorganism is provided. The method may include culturing the modified microorganism in a glucose-containing medium, and recovering 1,4-butanediol from the medium.

The step of culturing the modified microorganism may be performed under fermentation conditions.

The medium used to culture the cells may include any conventionally suitable medium known in the art for growing the host cells, such as minimal or complex media containing appropriate supplements. Suitable media are available from commercial suppliers or may be prepared according to published recipes (e.g., in catalogues of the American Type Culture Collection).

In an exemplary embodiment, the medium may be a fermentation medium containing sugars that can be fermented by a genetically modified microorganism. The sugar may be a hexose, for example, glucose, glycan or another polymer of glucose, a glucose oligomer, for example, maltose, maltotriose or isomaltotriose, panose, fructose or a fructose oligomer. In addition, the fermentation medium may contains nitrogen sources such as ammonia, ammonium sulfate, ammonium chloride, ammonium nitrate and urea; inorganic salts such as potassium monohydrogen phosphate, potassium dihydrogen phosphate and magnesium sulfate; and optionally a nutrient including various vitamin such as peptone, a meat extract, a yeast extract, a corn steep liquor, casamino acid, biotin and thiamine.

The modified microorganism may be cultured under batch, fed-batch or continuous fermentation conditions. Classical batch fermentation methods use a closed system, wherein the culture medium is made prior to the beginning of the fermentation run, the medium is inoculated with the desired organisms, and fermentation occurs without the subsequent addition of any components to the medium. In certain cases, the pH and oxygen content of the growth medium, but not the carbon source content, are altered during batch methods. The metabolites and cell biomass of the batch system change constantly up to the time the fermentation is stopped. In a batch system, cells usually progress through a static lag phase to a high growth log phase and finally to a stationary phase where growth rate is diminished or halted. If untreated, cells in the stationary phase eventually die. Generally, cells produce the most protein in the log phase.

A variation on the standard batch fermentation is a "fed-batch fermentation" system. In fed-batch fermentation, nutrients (e.g., a carbon source, nitrogen source, $O_2$, and typically, other nutrients) are only added when their concentration in culture falls below a threshold. Fed-batch systems are useful when catabolite repression is apt to inhibit the metabolism of the cells and where it is desirable to have limited amounts of nutrients in the medium. Actual nutrient concentration in fed-batch systems are estimated on the basis of the changes of measurable factors such as pH, dissolved oxygen and the partial pressure of waste gases such as $CO_2$. Batch and fed-batch fermentations are common and well known in the art.

Continuous fermentation employs an open system in which a defined culture medium is added continuously to a bioreactor and an equal amount of conditioned medium is removed simultaneously for processing. Continuous fermentation generally maintains the cultures at a constant high density where cells are primarily in log-phase growth. Continuous fermentation allows for the modulation of one factor or any number of factors that affect cell growth and/or end product concentration. For example, a limiting nutrient such as the carbon source or nitrogen source is maintained at a fixed rate and all other parameters are allowed to moderate. In other systems, a number of factors affecting growth are altered continuously while the cell concentration, measured by media turbidity, is kept constant. Continuous systems strive to maintain steady state growth conditions. Thus, cell loss due to medium being drawn off may be balanced against the cell growth rate in the fermentation. Methods of modulating nutrients and growth factors for continuous fermentation processes as well as techniques for maximizing the rate of product formation are known to those of skill in the art.

The step of recovering 1,4-butanediol from the medium may be performed by any suitable method. For example, the method may include salting-out, recrystallization, extraction with organic solvent, esterification distillation, chromatography, and electrodialysis, and the method for separation, purification, or collection may be appropriately selected according to the characteristics of the chemical.

Alternatively, the method may further include forming polybutylene succinate (PBS) from the recovered 1,4-butanediol. For example, PBS may be produced by condensation polymerization of the recovered 1,4-butanediol with succinic acid or dimethyl-succinate. The PBS is an aliphatic polyester-based polymer which has excellent biodegradability and formability. Therefore, the PBS may be used for fishing nets, films and packaging vessels.

Alternatively, the method may further include forming polybutylene terephthalate (PBT) from the recovered 1,4-butanediol. For example, PBT may be produced by condensation polymerization of the recovered 1,4-butanediol with terephthalic acid or dimethyl-terephthalate. The PBT is a polyester-based polymer which has excellent crystallinity, dimensional stability and formability. Therefore, the PBT may be used for electrical and electronics and automotive parts, and also used as an engineering plastic material.

Hereinafter, the invention will be described in further detail with respect to exemplary embodiments. However, it should be understood that the invention is not limited to these Examples and may be embodied in various modifications and changes.

EXAMPLES

Example 1

Identification of 1,4-butanediol-tolerant genes

C. glutamicum (C. glutamicum ATCC 13032), a 1,4-BOD-tolerant strain used to produce 1,4-butanediol at a high yield, was screened through random mutagenesis using a transposon (commercially available from EpiCentre, EZ-Tn5™ <R6Kγori/KAN-2>Tnp Transposome™ kit). As a result, an A48 strain in which a transcription regulatory factor, NCgl2886, was deleted, an F22 strain in which a GCN5-related N-acetyltransferase, NCgl2090, was deleted, an F66 strain in which a hypothetical protein, NCgl0224, was deleted, and a G65 strain in which a sugar phosphate isomerase/epimerase, NCgl2956, was deleted, were identified.

The A48, F22, F66 and G65 strains were deposited on May 11, 2012, under Accession Numbers KCTC12208BP, KCTC12209BP, KCTC12210BP and KCTC12211BP, respectively, with the Korean Collection for Type Cultures at the Korean Research Institute of Bioscience and Biotechnology (KRIBB) at 125 Gwahak-ro, Yuseong-gu, Daejeon 305-806 Republic of Korea. These deposits were made under the terms of the Budapest Treaty. To the extent required under 37 CFR 1.808, access to the deposits will be available during the pendency of any patent issuing from this patent application to persons determined by the Commissioner to be entitled thereto under 37 CFR 1.14 and 35 U.S.C. 122, and all restrictions imposed by the depositor on the availability to the public of the deposited biological material be irrevocably removed upon the granting of the patent.

Example 2

Measurement of the Growth Curve of the A48 Strain

The growth curve of the A48 strain identified in Example 1 was measured to determine whether the A48 strain had a difference in growth compared with the wild-type C. glutamicum ATCC 13032 in which the transcription regulatory factor gene NCgl2886 was not deleted.

The strain was pre-cultured at 30° C. for 16 hours, and the pre-cultured strain was seeded so that the absorbance (OD600) at 600 nm for the strain in 50 mL of an LB broth containing 80 g/L of 1,4-butanediol could reach 0.1. The seeded strain was cultured at 30° C. at 200 rpm, and measured for absorbance (OD600) at 600 nm at intervals of 3 hours to observe growth of the stain.

Figure 2:
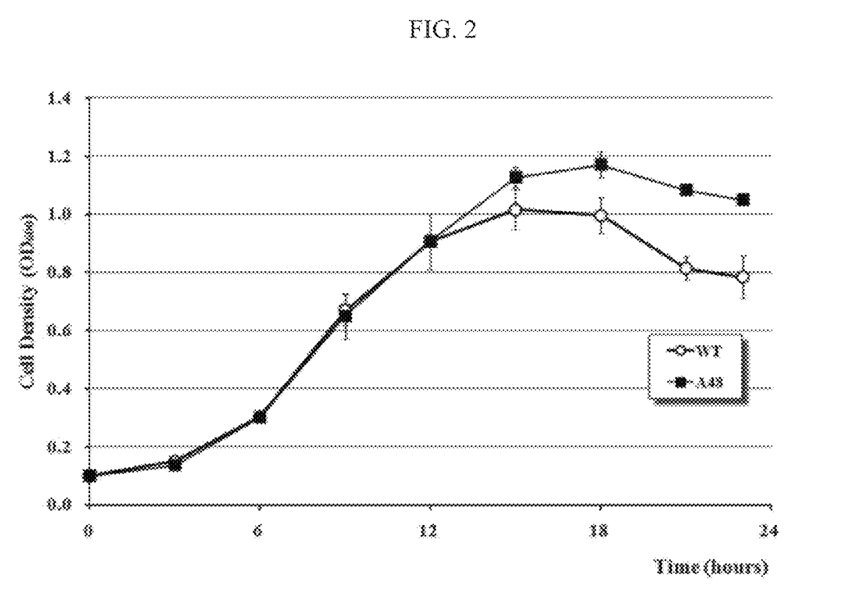
FIG. 2 is a graph illustrating the growth curve of an A48 strain as described in Example 2. Cell density (OD600) is indicated on the y-axis, and time (hours) is indicated on the x-axis.

The results are listed in the following Table 1 and shown in FIG. 2.

TABLE 1

| Strain | Growth Rate | Maximum Population |
|---|---|---|
| A48 | 0.95 (−5%) | 1.15 (+15%) |

Example 3

Measurement of the Growth Curves of the F22, F66 and G65 Strains

The growth curves of the F22, F66 and G65 strains identified in Example 1 were measured to determine whether the strains had a difference in growth compared with the wild-type C. glutamicum ATCC 13032.

Each of the strains was pre-cultured at 30° C. for 16 hours, and each of the pre-cultured strains was seeded so that the absorbance (OD600) at 600 nm for the strain in 50 mL of an LB broth containing 80 g/L of 1,4-butanediol could reach 0.1. Each of the seeded strains was cultured at 30° C. at 200 rpm, and measured for absorbance (OD600) at 600 nm at intervals of 2 to 18 hours to observe growth of the stains.

Figure 3:
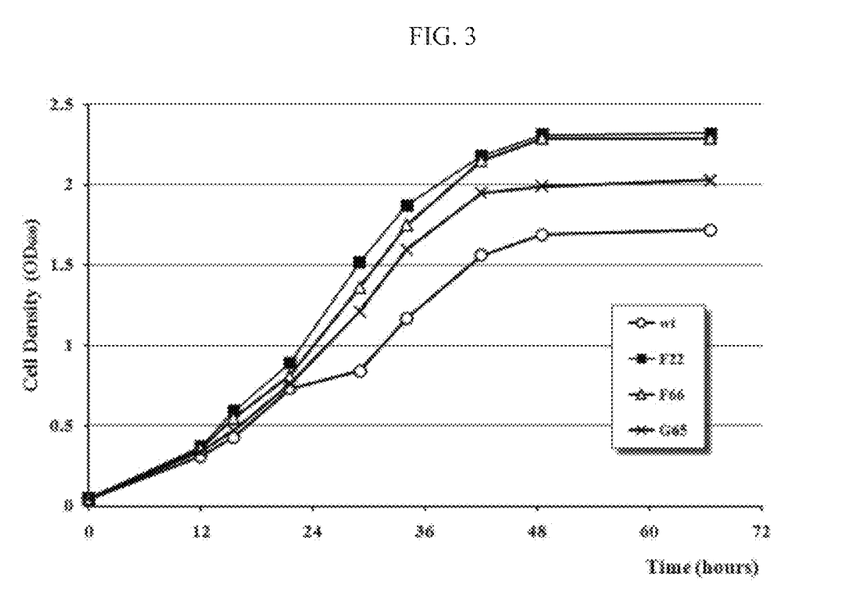
FIG. 3 is a graph illustrating the growth curves of F22, F66 and G65 strains as described in Example 3. Cell density (OD600) is indicated on the y-axis, and time (hours) is indicated on the x-axis.

The results are listed in the following Table 2 and shown in FIG. 3.

TABLE 2

| Strain | Growth Rate | Maximum Population |
|---|---|---|
| F22 | 1.36 (+36%) | 1.35 (+35%) |
| F66 | 1.43 (+43%) | 1.38 (+38%) |
| G65 | 1.26 (+26%) | 1.18 (+18%) |

Figure 4:
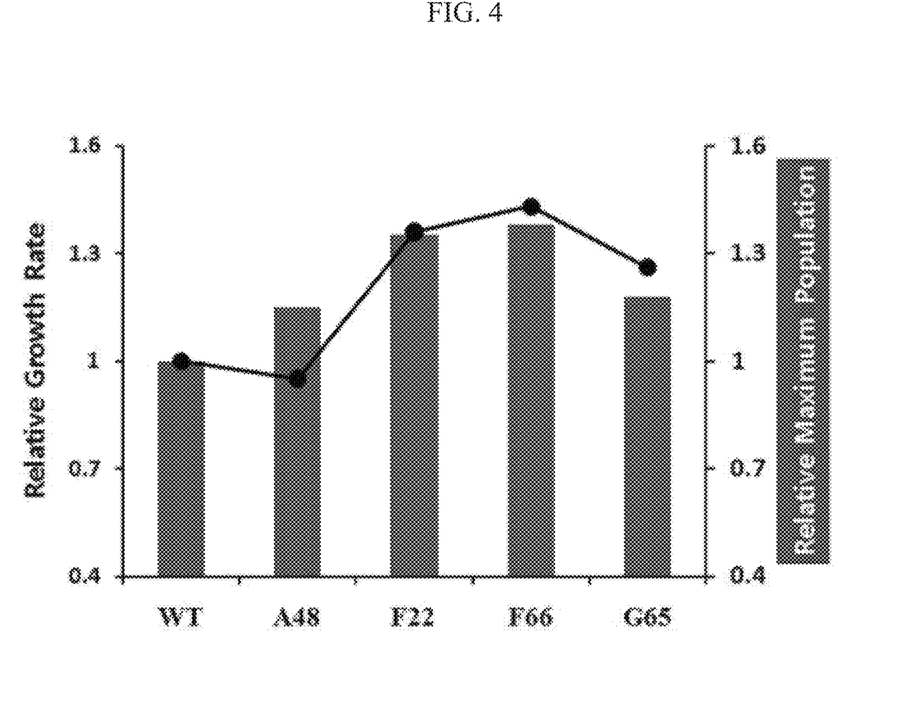
FIG. 4 is a graph illustrating the relative growth curves of the A48, F22, F66 and G65 strains. Relative growth rate/relative maximum population is indicated on the y-axis, and the particular strains are indicated on the x-axis.

From the overall results of Examples 2 and 3, the relative growth rate and maximum population are shown in FIG. 4.

As shown in FIG. 4, the mutant C. glutamicum strains according to the exemplary embodiments had an increased relative growth rate and maximum population compared with the wild-type strain. That is, it could be seen that 1,4-butanediol could be produced at a high yield even when 1,4-butanediol was present at a high concentration.

While exemplary embodiments have been disclosed herein, it should be understood that other variations may be possible. Such variations are not to be regarded as a departure from the spirit and scope of exemplary embodiments of the present application, and all such modifications as would be obvious to one skilled in the art are intended to be included within the scope of the following claims.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A modified microorganism for producing a high yield of 1,4-butanediol, wherein the modified microorganism comprises disruption or deletion of a gene encoding at least one selected from the group consisting of transcription regulatory factor NCgl2886, GCN5-related N-acetyltransferase NCgl2090, hypothetical protein NCgl0224 and sugar phosphate isomerase/epimerase NCgl2956.

2. The modified microorganism of claim 1, wherein the modified microorganism is selected from the group consisting of *Escherichia, Klebsiella, Bacillus, Corynebacterium, Zymomonas, Lactococcus, Lactobacillus, Streptomyces, Clostridium, Pseudomonas, Alcaligenes, Salmonella, Shigella, Burkholderia, Aspergillus, Oligotropha, Pichia, Candida, Hansenula, Saccharomyces* and *Kluyveromyces*.

3. The modified microorganism of claim 1, wherein the modified microorganism is *Corynebacterium glutamicum*.

4. The modified microorganism of claim 1, wherein the gene is heterologous to the modified microorganism.

5. The modified microorganism of claim 4, wherein the gene is derived from the group consisting of *Escherichia coli, Saccharomyces cerevisiae, Clostridium kluyveri, Clostridium acetobutylicum, Clostridium beijerinckii, Clostridium saccharoperbutylacetonicum, Clostridium perfringens, Clostridium difficile, Ralstonia eutropha, Mycobacterium bovis, Mycobacterium tuberculosis, Porphyromonas gingivalis* and *Corynebacterium glutamicum*.

6. The modified microorganism of claim 1, wherein the gene encoding transcription regulatory factor NCgl2886 comprising the amino acid sequence of SEQ ID NO: 1, or a sequence with at least about 70% sequence identity to the amino acid sequence of SEQ ID NO: 1, is deleted or disrupted.

7. The modified microorganism of claim 1, wherein the gene encoding GCN5-related N-acetyltransferase NCgl2090 comprising the amino acid sequence of SEQ ID NO: 2, or a sequence with at least about 70% sequence identity to the amino acid sequence of SEQ ID NO: 2, is deleted or disrupted.

8. The modified microorganism of claim 1, wherein the gene encoding hypothetical protein NCgl0224 comprising the amino acid sequence of SEQ ID NO: 3, or a sequence with at least about 70% sequence identity to the amino acid sequence of SEQ ID NO: 3, is deleted or disrupted.

9. The modified microorganism of claim 1, wherein the gene encoding sugar phosphate isomerase/epimerase NCgl2956 comprising the amino acid sequence of SEQ ID NO: 4, or a sequence with at least about 70% sequence identity to the amino acid sequence of SEQ ID NO: 4, is deleted or disrupted.

10. The modified microorganism of claim 1, wherein the gene is deleted or disrupted by gene manipulation, enforced silencing, mutagenesis, or screening.

11. The modified microorganism of claim 10, wherein the gene is deleted or disrupted by insertion of a transposon.

12. The modified microorganism of claim 1, wherein a growth rate of the modified microorganism is increased compared with a wild-type microorganism.

13. The modified microorganism of claim 12, wherein a growth rate of the modified microorganism is increased by 25% or more compared with the wild-type microorganism.

14. The modified microorganism of claim 1, wherein the modified microorganism is selected from the group consisting of strains deposited under accession number KCTC12208BP, KCTC12209BP, KCTC12210BP and KCTC12211BP with the Korean Collection for Type Cultures at the Korean Research Institute of Bioscience and Biotechnology (KRIBB) at 125 Gwahak-ro, Yuseong-gu, Daejeon 305-806 Republic of Korea.

15. A method of producing 1,4-butanediol, comprising:
culturing the modified microorganism of claim 1 in a glucose-containing medium; and
recovering the 1,4-butanediol from the medium.

16. A method of producing polybutylene succinate (PBS), comprising:
culturing the modified microorganism of claim 1 in a glucose-containing medium;
recovering the 1,4-butanediol from the medium; and
performing condensation polymerization of the recovered 1,4-butanediol with succinic acid or dimethyl-succinate, thereby producing PBS.

17. A method of producing polybutylene terephthalate (PBT), comprising:
culturing the modified microorganism of claim 1 in a glucose-containing medium;
recovering the 1,4-butanediol from the medium; and
performing condensation polymerization of the recovered 1,4-butanediol with terephthalic acid or dimethyl-terephthalate,
thereby producing PBT.

18. A method of increasing the yield of 1,4-butanediol from a microorganism, the method comprising deleting or disrupting the expression of transcription regulatory factor NCgl2886, GCN5-related N-acetyltransferase NCgl2090, hypothetical protein NCgl0224, or sugar phosphate isomerase/epimerase NCgl2956 in the microorganism, whereby the 1,4-butanediol yield of the microorganism is increased as compared to a wild-type microorganism of the same kind.

* * * * *